United States Patent
Li et al.

(10) Patent No.: US 8,433,382 B2
(45) Date of Patent: Apr. 30, 2013

(54) TRANSMISSION MODE PHOTON DENSITY WAVE SYSTEM AND METHOD

(75) Inventors: Youzhi Li, Longmont, CO (US); Andy S. Lin, Boulder, CO (US); Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 904 days.

(21) Appl. No.: 12/512,127

(22) Filed: Jul. 30, 2009

(65) Prior Publication Data
US 2010/0081897 A1 Apr. 1, 2010

Related U.S. Application Data

(63) Continuation-in-part of application No. 12/241,160, filed on Sep. 30, 2008.

(51) Int. Cl.
*A61B 5/1455* (2006.01)

(52) U.S. Cl.
USPC .......................................... 600/310; 600/476

(58) Field of Classification Search .................. 600/310, 600/322, 323, 336, 473, 476
See application file for complete search history.

(56) References Cited

U.S. PATENT DOCUMENTS

| | | |
|---|---|---|
| 3,638,640 A | 2/1972 | Shaw |
| 4,223,680 A | 9/1980 | Jöbsis |
| 4,281,645 A | 8/1981 | Jöbsis |
| 4,321,930 A | 3/1982 | Jöbsis et al. |
| 4,714,341 A | 12/1987 | Hamaguri et al. |
| 4,805,623 A | 2/1989 | Jöbsis |
| 4,807,631 A | 2/1989 | Hersh et al. |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |

(Continued)

FOREIGN PATENT DOCUMENTS

| | | |
|---|---|---|
| AU | 732799 B2 | 5/2001 |
| DE | 69123448 | 5/1997 |

(Continued)

OTHER PUBLICATIONS

D.J. Pine, et al.; "Diffusing-Wave Spectroscopy," *The American Physical Society*, vol. 60, No. 12, Mar. 1988, pp. 1134-1137.

(Continued)

*Primary Examiner* — Eric Winakur
(74) *Attorney, Agent, or Firm* — Fletcher Yoder

(57) ABSTRACT

Present embodiments are directed to a monitor system, such as a pulse oximetry system. The system may include a detection feature, an emission feature capable of emitting light into tissue and arranged relative to the detection feature such that the detection feature is capable of detecting the light from the tissue after passing generally through a portion of the tissue, a modulator capable of modulating the light to generate photon density waves at a modulation frequency generally in a range of 50 MHz to 3 GHz, a detector communicatively coupled with the detection feature, wherein the detector is capable of detecting characteristics of the photon density waves comprising amplitude changes and phase shifts, and a processor capable of making determinations relating to a value of a physiologic parameter of the tissue based at least in part on the detected characteristics.

20 Claims, 6 Drawing Sheets

U.S. PATENT DOCUMENTS

| | | | |
|---|---|---|---|
| 5,028,787 A | 7/1991 | Rosenthal et al. | |
| 5,065,749 A | 11/1991 | Hasebe et al. | |
| 5,084,327 A | 1/1992 | Stengel | |
| 5,088,493 A | 2/1992 | Giannini et al. | |
| 5,119,815 A | 6/1992 | Chance | |
| 5,122,974 A | 6/1992 | Chance | |
| 5,167,230 A | 12/1992 | Chance | |
| 5,187,672 A | 2/1993 | Chance et al. | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,497,769 A | 3/1996 | Gratton et al. | |
| 5,553,614 A | 9/1996 | Chance | |
| 5,555,885 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Kuenstner | |
| 5,730,124 A | 3/1998 | Yamauchi | |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,058,324 A * | 5/2000 | Chance | 600/473 |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,192,261 B1 | 2/2001 | Gratton et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,322,515 B1 | 11/2001 | Goor et al. | |
| 6,352,502 B1 | 3/2002 | Chaiken et al. | |
| 6,353,750 B1 | 3/2002 | Kimura et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,516,209 B2 | 2/2003 | Cheng et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,801,648 B2 | 10/2004 | Cheng | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,850,053 B2 | 2/2005 | Daalmans et al. | |
| 6,859,658 B1 | 2/2005 | Krug | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,006,676 B1 | 2/2006 | Zeylikovich et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,090,648 B2 | 8/2006 | Sackner et al. | |
| 7,127,278 B2 | 10/2006 | Melker et al. | |
| 7,162,306 B2 | 1/2007 | Caby et al. | |
| 7,164,938 B2 | 1/2007 | Geddes et al. | |
| 7,209,775 B2 | 4/2007 | Bae et al. | |
| 7,236,811 B2 | 6/2007 | Schmitt | |
| 7,263,395 B2 | 8/2007 | Chan et al. | |
| 7,272,426 B2 | 9/2007 | Schmid | |
| 7,330,746 B2 | 2/2008 | Demuth et al. | |
| 7,373,193 B2 | 5/2008 | Al-Ali et al. | |
| 7,375,347 B2 | 5/2008 | Colvin et al. | |
| 7,378,954 B2 | 5/2008 | Wendt | |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |

| | | | |
|---|---|---|---|
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0144584 A1 | 7/2003 | Mendelson | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0230106 A1 | 11/2004 | Schmitt et al. | |
| 2005/0080323 A1 | 4/2005 | Kato | |
| 2005/0101850 A1 | 5/2005 | Parker | |
| 2005/0113651 A1 | 5/2005 | Wood et al. | |
| 2005/0113656 A1 | 5/2005 | Chance | |
| 2005/0168722 A1 | 8/2005 | Forstner et al. | |
| 2005/0177034 A1 | 8/2005 | Beaumont | |
| 2005/0192488 A1 | 9/2005 | Bryenton et al. | |
| 2005/0197583 A1 | 9/2005 | Chance | |
| 2005/0203357 A1 | 9/2005 | Debreczeny et al. | |
| 2005/0209516 A1 | 9/2005 | Fraden | |
| 2005/0228248 A1 | 10/2005 | Dietiker | |
| 2005/0267346 A1 | 12/2005 | Faber et al. | |
| 2005/0283059 A1 | 12/2005 | Iyer et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0052680 A1 | 3/2006 | Diab | |
| 2006/0058595 A1 | 3/2006 | Herrmann | |
| 2006/0058683 A1 | 3/2006 | Chance | |
| 2006/0063995 A1 | 3/2006 | Yodh et al. | |
| 2006/0064024 A1 | 3/2006 | Schnall | |
| 2006/0122475 A1 | 6/2006 | Balberg et al. | |
| 2006/0129037 A1 | 6/2006 | Kaufman et al. | |
| 2006/0129038 A1 | 6/2006 | Zelenchuk et al. | |
| 2006/0195028 A1 | 8/2006 | Hannula et al. | |
| 2006/0224058 A1 | 10/2006 | Mannheimer | |
| 2006/0247501 A1 | 11/2006 | Ali | |
| 2006/0247506 A1 | 11/2006 | Balberg et al. | |
| 2006/0258921 A1 | 11/2006 | Addison et al. | |
| 2007/0093702 A1 | 4/2007 | Yu et al. | |
| 2008/0139908 A1 | 6/2008 | Kurth | |
| 2008/0200823 A1 | 8/2008 | Cho et al. | |
| 2008/0312533 A1 | 12/2008 | Balberg et al. | |

FOREIGN PATENT DOCUMENTS

| | | |
|---|---|---|
| DE | 19640807 | 9/1997 |
| EP | 0194105 | 9/1986 |
| EP | 0826958 A2 | 3/1998 |
| JP | 3124073 | 5/1991 |
| JP | 3170866 | 7/1991 |
| JP | 3238813 | 10/1991 |
| JP | 4191642 | 7/1992 |
| JP | 4332536 | 11/1992 |
| JP | 5049624 | 3/1993 |
| JP | 7124138 | 5/1995 |
| JP | 10216115 | 9/1998 |
| JP | 11019074 | 1/1999 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004194908 | 7/2004 |
| JP | 2004202190 | 7/2004 |
| JP | 2004248819 | 9/2004 |
| JP | 2004290544 | 10/2004 |
| JP | 2004290545 | 10/2004 |
| WO | WO9101678 | 2/1991 |
| WO | WO9200513 | 1/1992 |
| WO | WO9221281 | 12/1992 |
| WO | WO9309711 | 5/1993 |
| WO | WO9313706 A2 | 7/1993 |
| WO | WO93/16629 | 9/1993 |
| WO | WO9403102 | 2/1994 |
| WO | WO9512349 | 5/1995 |
| WO | WO9749330 | 12/1997 |
| WO | WO9817174 | 5/1998 |
| WO | WO98/42249 | 10/1998 |
| WO | WO98/42251 | 10/1998 |
| WO | WO9843071 | 10/1998 |
| WO | WO9932030 | 7/1999 |
| WO | WO0021438 | 4/2000 |
| WO | WO0140776 | 6/2001 |
| WO | WO03077750 | 9/2003 |
| WO | WO 03/102558 A1 | 12/2003 |
| WO | WO2004010844 | 2/2004 |
| WO | WO2005009221 | 2/2005 |
| WO | WO2005064314 A1 | 7/2005 |
| WO | WO2007051066 | 5/2007 |
| WO | WO 2010/039418 A2 | 4/2010 |

OTHER PUBLICATIONS

D.J. Pine, et al.; "Diffusing-wave spectroscopy: dynamic light scattering in the multiple scattering limit," *J. Phys. France*, vol. 51, Sep. 1990, pp. 2101-2127.

X.L. Wu, et al.; "Diffusing-wave spectroscopy in a shear flow," *J. Opt. Soc. Am. B.*, vol. 7, No. 1, Jan. 1990, pp. 15-20.

J.M. Schmitt, et al.; "Interference of diffusive light waves," *J. Opt. Soc. Am. A.*, vol. 9, No. 10 (Oct. 1992), pp. 1832-1843.

Aoyagi, T., et al.; "Analysis of Motion Artifacts in Pulse Oximetry," Japanese Society ME, vol. 42, p. 20 (1993) (Article in Japanese—contains English summary of article).

D.A. Weitz, et al.; "Diffusing-Wave Spectroscopy: The Technique and Some Applications," *Physica Scripta*, vol. T49, 1993, pp. 610-621.

Barreto, A.B., et al.; "Adaptive Cancelation of Motion artifact in Photoplethysmographic Blood Volume Pulse Measurements for Exercise Evaluation," IEEE-EMBC and CMBEC—Theme 4: Signal Processing, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," Journal of clinical Monitoring, vol. 13, pp. 109-113 (1997).

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

Poets, C. F., et al.; "Detection of movement artifact in recorded pulse oximeter saturation," Eur. J. Pediatr.; vol. 156, pp. 808-811 (1997).

Masin, Donald I., et al.; "Fetal Transmission Pulse Oximetry," Proceedings 19th International Conference IEEE/EMBS, Oct. 30-Nov. 2, 1997; pp. 2326-2329.

Nijland, Roel, et al.; "Validation of Reflectance Pulse Oximetry: An Evaluation of a new Sensor in Piglets," Journal of Clinical Monitoring, vol. 13, pp. 43-49 (1997).

Nogawa, Masamichi, et al.; "A New Hybrid Reflectance Optical Pulse Oximetry Sensor for Lower Oxygen Saturation Measurement and for Broader Clinical Application," SPIE, vol. 2976, pp. 78-87 (1997).

Mannheimer, Paul D., et al.; "Wavelength Selection for Low-Saturation Pulse Oximetry," IEEE Transactions on Biomedical Engineering, vol. 44, No. 3, pp. 148-158 (Mar. 1997).

Buschman, J.P., et al.; "Principles and Problems of Calibration of Fetal Oximeters," Biomedizinische Technik, vol. 42, pp. 265-266 (1997).

Leahy, Martin J., et al.; "Sensor Validation in Biomedical Applications," IFAC Modelling and Control in Biomedical Systems, Warwick, UK; pp. 221-226 (1997).

Barreto, Armando B., et al.; "Adaptive LMS Delay Measurement in dual Blood Volume Pulse Signals for Non-Invasive Monitoring," IEEE, pp. 117-120 (1997).

East, Christine E., et al.; "Fetal Oxygen Saturation and Uterine Contractions During Labor," American Journal of Perinatology, vol. 15, No. 6, pp. 345-349 (Jun. 1998).

Hayes, Matthew J., et al.; "Quantitative evaluation of photoplethysmographic artifact reduction for pulse oximetry," SPIE, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International conference of the IEEE Engie in Medicine and Biology Society, vol. 20, No. 6, p. 3072-3075, 1998.

Hayes, Matthew J., et al.; "Artifact reduction in photoplethysmography," Applied Optics, vol. 37, No. 31, pp. 7437-7446 (Nov. 1998).

S.E. Skipetrov, et al.; "Diffusing-wave spectroscopy in randomly inhomogeneous media with spatially localized scatterer flows," *Journal of Experimental and Theoretical Physics*, vol. 86, No. 4, Apr. 1998, pp. 661-665.

Such, Hans Olaf; "Optoelectronic Non-invasive Vascular Diagnostics Using multiple Wavelength and Imaging Approach," Dissertation, (1998).

Lutter, N., et al.; "Comparison of Different Evaluation Methods for a Multi-wavelength Pulse Oximeter," Biomedizinische Technik, vol. 43, (1998).

Z.L. Wu, et al.; "Laser modulated scattering as a nondestructive evaluation tool for defect inspection in optical materials for high power laser applications," *Optics Express*, vol. 3, No. 10; Nov. 1998, pp. 376-383.

Todd, Bryan, et al.; "The Identification of Peaks in Physiological Signals," Computers and Biomedical Research, vol. 32, pp. 322-335 (1999).

G. Popescu, et al.; "Optical path-length spectroscopy of wave propagation in random media," *Optics Letters*, vol. 24, No. 7, Apr. 1999, pp. 442-444.

Rhee, Sokwoo, et al.; "Design of a Artifact-Free Wearable Plethysmographic Sensor," Proceedings of the First joint BMES/EMBS Conference, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," Journal of clinical Anestesia, vol. 11, pp. 192-195 (1999).

Kaestle, S.; "An Algorithm for Reliable Processing of Pulse Oximetry Signals Under strong Noise Conditions," Dissertation Book, Lubeck University, Germany (1999).

Seelbach-Göbel, Birgit, et al.; "The prediction of fetal acidosis by means of intrapartum fetal pulse oximetry," Am J. Obstet. Gynecol., vol. 180, No. 1, Part 1, pp. 73-81 (1999).

Goldman, Julian M.; "Masimo Signal Extraction Pulse Oximetry," Journal of Clinical Monitoring and Computing, vol. 16, pp. 475-483 (2000).

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Al. N. Korolevich, et al.: "Experimental study of the potential use of diffusing wave spectroscopy to investigate the structural characteristics of blood under multiple scattering," *Bioelectrochemistry*, vol. 52, 2000, pp. 223-227.

V. Ntziachristos, et al.; "Oximetry based on diffuse photon density wave differentials," *Am. Assoc. Phys. Med.*, vol. 27, No. 2, Feb. 2000, pp. 410-521.

Yao, Jianchu, et al.; "Design of a Plug-and-Play Pulse Oximeter," Proceedings of the Second Joint EMBS/BMES Conference, Houston, Texas, Oct. 23-26, 2002; pp. 1752-1753.

Kaestle, S.; "Determining Artefact Sensitivity of New Pulse Oximeters in Laboratory Using Signals Obtained from Patient," Biomedizinische Technik, vol. 45 (2000).

Cysewska-Sobusaik, Anna; "Metrological Problems With noninvasive Transillumination of Living Tissues," Proceedings of SPIE, vol. 4515, pp. 15-24 (2001).

Belal, Suliman Yousef, et al.; "A fuzzy system for detecting distorted plethysmogram pulses in neonates and paediatric patients," Physiol. Meas., vol. 22, pp. 397-412 (2001).

Hayes, Matthew J., et al.; "A New Method for Pulse Oximetry Possessing Inherent Insensitivity to Artifact," IEEE Transactions on Biomedical Engineering, vol. 48, No. 4, pp. 452-461 (Apr. 2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Gehring, Harmut, et al.; "The Effects of Motion Artifact and Low Perfusion on the Performance of a New Generation of Pulse Oximeters in Volunteers Undergoing Hypoxemia," Respiratory Care, Vo. 47, No. 1, pp. 48-60 (Jan. 2002).

Jopling, Michae W., et al.; "Issues in the Laboratory Evaluation of Pulse Oximeter Performance," Anesth Analg, vol. 94, pp. S62-S68 (2002).

Lutter, N., et al.; "Accuracy of Noninvasive Continuous Blood Pressure; Measurement Utilising the Pulse Transit Time," Journal of clinical Monitoring and Computing, vol. 17, Nos. 7-8, pp. 469 (2002).

Gostt, R., et al.; "Pulse Oximetry Artifact Recognition Algorithm for Computerized Anaesthetic Records," Journal of Clinical Monitoring and Computing Abstracts, p. 471 (2002).

Chan, K.W., et al.; "17.3: Adaptive Reduction of Motion Artifact from Photoplethysmographic Recordings using a Variable Step-Size LMS Filter," IEEE, pp. 1343-1346 (2002).

Yamaya, Yoshiki, et al.; "Validity of pulse oximetry during maximal exercise in normoxia, hypoxia, and hyperoxia," J. Appl. Physiol., vol. 92, pp. 162-168 (2002).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Yoon, Gilwon, et al.; Multiple diagnosis based on Photoplethysmography: hematocrit, SpO2, pulse and respiration, Optics in Health Care and Biomedical optics: Diagnostics and Treatment; Proceedings of the SPIE, vol. 4916; pp. 185-188 (2002).

Tremper, K.K.; "A Second Generation Technique for Evaluating Accuracy and Reliability of Second Generation Pulse Oximeters," Journal of Clinical Monitoring and Computing, vol. 16, pp. 473-474 (2000).

Lopez-Silva, Sonnia Maria Lopez, et al.; "Near-infrared transmittance pulse oximetry with laser diodes," Journal of Biomedical Optics, vol. 8, No. 3, pp. 525-533 (Jul. 2003).

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Stetson, Paul F.; "Determining Heart Rate from Noisey Pulse Oximeter Signals Using Fuzzy Logic," The IEEE International Conference on Fuzzy Systems, St. Louis, Missouri, May 25-28, 2003; pp. 1053-1058.

Aoyagi, Takuo; "Pulse oximetry: its invention, theory, and future," Journal of Anesthesia, vol. 17, pp. 259-266 (2003).

Lee, C.M., et al.; "Reduction of motion artifacts from photoplethysmographic recordings using wavelet denoising approach," IEEE EMBS Asian-Pacific Conference on Biomedical Engineering, Oct. 20-22, 2003; pp. 194-195.

A. Johansson; "Neural network for photoplethysmographic respiratory rate monitoring," Medical & Biological Engineering & Computing, vol. 41, pp. 242-248 (2003).

Lopez-Silva, S.M., et al.; "Transmittance Photoplethysmography and Pulse Oximetry With Near Infrared Laser Diodes," IMTC 2004—Instrumentation and Measurement Technology Conference, Como, Italy, May 18-20, 2004; pp. 718-723.

Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," Proceedings of the 26th Annual International conference of the IEEE EMBS, San Francisco, California, Sep. 2004, pp. 2153-2156.

Matsuzawa, Y., et al.; "Pulse Oximeter," Home Care Medicine, pp. 42-45 (Jul. 2004); (Article in Japanese—contains English summary of article).

Crespi, F., et al.; "Near infrared oxymeter prototype for non-invasive analysis of rat brain oxygenation," Optical Sensing, Proceedings of SPIE, vol. 5459, pp. 38-45 (2004).

Yan, Yong-sheng, et al.; "Reduction of motion artifact in pulse oximetry by smoothed pseudo Wigner-Ville distribution," Journal of NeuroEngineering and Rehabilitation, vol. 2, No. 3 (9 pages) (Mar. 2005).

F. Jaillon, et al.; "Diffusing-wave spectroscopy from head-like tissue phantoms: influence of a non-scattering layer," *Optics Express*, vol. 14, No. 22; Oct. 2006, pp. 10181-10194.

G. Dietsche, et al.; "Fiber-based multispeckle detection for time-resolved diffusing-wave spectroscopy: characterization and application to blood flow detection in deep tissue," *Applied Optics*, vol. 46, No. 35; Dec. 2007, pp. 8506-8514.

J. Huang, et al.; "Low Power Motion Tolerant Pulse Oximetry," Abstracts, A7, p. S103. (undated).

P. Lang, et al.; "Signal Identification and Quality Indicator™ for Motion Resistant Pulse Oximetry," Abstracts, A10, p. S105. (undated).

Hamilton, Patrick S., et al.; "Effect of Adaptive Motion-Artifact Reduction on QRS Detection," Biomedical Instrumentation & Technology, pp. 197-202 (undated).

Kim, J.M., et al.; "Signal Processing Using Fourier & Wavelet Transform," pp. II-310-II-311 (undated).

R. Neumann, et al.; "Fourier Artifact suppression Technology Provides Reliable SpO2," Abstracts, A11, p. S105. (undated).

Odagiri, Y.; "Pulse Wave Measuring Device," Micromechatronics, vol. 42, No. 3, pp. 6-11 (undated) (Article in Japanese—contains English summary of article).

J.M. Tualle, et al.; "Time-Resolved Diffusing Wave Spectroscopy for selected photon paths beyond 300 transport mean free paths," White Paper (undated).

Yamazaki, Nakaji, et al.; "Motion Artifact Resistant Pulse Oximeter (Durapulse PA 2100)," Journal of Oral Cavity Medicine, vol. 69, No. 4, pp. 53 (date unknown) (Article in Japanese—contains English summary of article).

International Search Report PCT/US2010/037571, 4 pages, mailed Dec. 17, 2010.

* cited by examiner

TRANSMISSION MODE PHOTON DENSITY WAVE SYSTEM AND METHOD

CROSS REFERENCE TO RELATED APPLICATIONS

This application is a continuation-in-part of U.S. patent application Ser. No. 12/241,160, which was filed on Sep. 30, 2008, and is hereby incorporated by reference in its entirety for all purposes.

BACKGROUND

The present disclosure relates generally to a photon density wave system, and, more particularly, to apparatus of a transmission mode photon density wave system.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Pulse oximetry may be defined as a non-invasive technique that facilitates monitoring of a patient's blood flow characteristics. For example, pulse oximetry may be used to measure blood oxygen saturation of hemoglobin in a patient's arterial blood and/or the patient's heart rate. Specifically, these blood flow characteristic measurements may be acquired using a non-invasive sensor that passes light through a portion of a patient's tissue and photo-electrically senses the absorption and scattering of the light through the tissue. Typical pulse oximetry technology currently utilizes two light emitting diodes (LEDs) and a single optical detector to measure pulse and oxygen saturation of a given tissue bed.

A typical signal resulting from the sensed light may be referred to as a plethysmographic waveform. Such measurements are largely based on absorption of emitted light by specific types of blood constituents. Once acquired, this measurement may be used with various algorithms to estimate a relative amount of blood constituent in the tissue. For example, such measurements may provide a ratio of oxygenated to deoxygenated hemoglobin in the volume being monitored. It should be noted that the amount of arterial blood in the tissue is generally time varying during a cardiac cycle, which is reflected in the plethysmographic waveform.

The accuracy of blood flow characteristic estimation via pulse oximetry depends on a number of factors. For example, variations in light absorption characteristics can affect accuracy depending on where the sensor is located and/or the physiology of the patient being monitored. Additionally, various types of noise and interference can create inaccuracies. For example, electrical noise, physiological noise, and other interference can contribute to inaccurate blood flow characteristic estimates. Some sources of noise are consistent, predictable, and/or minimal, while some sources of noise are erratic and cause major interruptions in the accuracy of blood flow characteristic measurements. Accordingly, it is desirable to enable more accurate and/or controlled measurement of physiologic parameters by providing a system and method that addresses inconsistencies in physiologic characteristics of patients and issues relating to noise.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
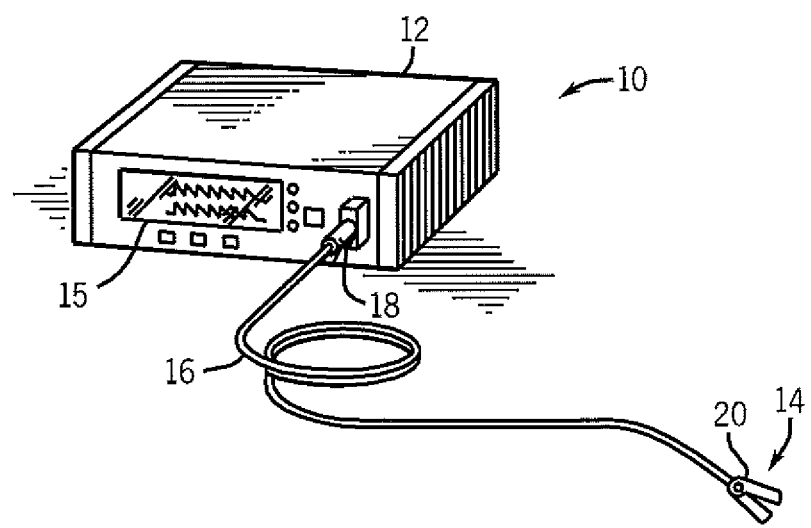
FIG. 1 illustrates a perspective view of a transmission mode pulse oximeter system capable of utilizing photon density waves in accordance with present embodiments.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to non-invasively measuring physiologic parameters corresponding to blood flow in a patient by emitting light into a patient's tissue with light emitters (e.g., lasers/LEDs) and photoelectrically detecting the light after it has passed through the patient's tissue. More specifically, present embodiments are directed to modulate the emitted light at high frequencies to generate resolvable photon density waves. Photon density waves may be described as progressively decaying waves of intensity. On a microscopic level, photons generated by a light source generally make random migrations in a scattering medium. However, the photons collectively form a photon density wave at a modulation frequency that moves away from the light source. Photon propagation is generally dictated by scattering and absorption in the medium through which the waves are moving. Like other waves, photon density waves undergo refraction, diffraction, interference, dispersion, attenuation, and so forth.

Phase changes and amplitude changes in the photon density waves after passing through a medium may be detected to facilitate measurement of changes in total scattering particles and absorber concentration, respectively, in the observed medium. Indeed, the phase of such waves may be sensitive to scattering and the amplitude of such waves may be sensitive to absorption. For example, detection of phase changes in the photon density waves generated by modulation at high frequency may correspond to total hemoglobin because the wavelength of the photon density waves may be shorter than an average absorption length of photons. Thus, detected variations in the phase may be predominantly due to the scattering coefficient and not absorption. In other words, the variation in phase may be predominantly due to the total number of scattering particles (e.g., total hemoglobin) in the observed medium and not merely a ratio of particles (e.g., oxygenated and deoxygenated hemoglobin) that absorb different colors of light. On the other hand, changes in the amplitude of the photon density waves may correspond to absorption of specific light color (e.g. red or infrared light) in the observed volume, and, thus, a ratio of different types of particles (e.g., oxygenated and deoxygenated hemoglobin) in the probed medium.

In addition to the features set forth above, it should also be noted that present embodiments may relate to emitting multiple high frequency photon density waves in coordination with one another to focus on certain tissue areas (e.g., regions rich with pulsatile signals), to facilitate identification of noise artifacts, to address patient specific tissue characteristics (e.g., skin color and low blood oxygen saturation levels), and/or to reduce noise in general. For example, multiple photon density waves may be emitted in patterns such that the waves build on one another to focus intensity at certain points throughout a tissue bed. In a specific example, a tissue bed may be swept with combinations of emission frequencies to identify areas rich with pulsatile signals. Similarly, waves may be emitted such that the waves cancel one another out in a substantially noise-free environment. Thus, detection of the waves that have not been canceled out may be indicative of the presence of noise. Additionally, relative measurements may be utilized to identify and/or correct noise. For example, certain wave features may be detected at multiple detector locations and compared to one another to identify characteristics such as venous pulsation noise.

FIG. 1 illustrates a perspective view of a pulse oximetry system 10 in accordance with some embodiments. The system 10 includes a pulse oximeter or monitor 12 that communicatively couples to a sensor 14. The monitor 12 may include a display 15, a memory, a processor, and various monitoring and control features. The sensor 14 may include a sensor cable 16, a connector plug 18, and a sensor assembly or body 20 configured to attach to a patient (e.g., a patient's finger, ear, lip, or toe) in a manner that facilitates transmission of light through the patient's tissue from one side to another. The system 10 may be utilized to observe the blood constituents of a patient's arterial blood to facilitate estimation of the state of oxygen exchange in the patient's body by emitting waves into tissue and detecting the waves after dispersion and/or reflection by the tissue. The amount of light that passes through the tissue and other characteristics of light waves may vary in accordance with the changing amount of certain blood constituents in the tissue and the related light absorption and/or scattering. For example, as with conventional pulse oximeter systems, the system 10 may emit light from two or more LEDs or lasers into pulsatile tissue and then detect the transmitted light with a light detector (e.g., a photodiode or photodetector) after the light has passed through the pulsatile tissue. Such measurements may be utilized to estimate a percentage of blood oxygen saturation in the probed volume of blood. Additionally, in accordance with present embodiments, the system 10 may modulate the emitted light to generate photon density waves at a high frequency such that phase shifts may be detected that correlate predominantly to scattering particles in the probed volume of blood.

As generally indicated above, the system 10 may generate and detect light waves to facilitate non-invasive measurement of a patient's physiological characteristics. In embodiments, the system 10 may generate resolvable photon density waves and make relative measurements of certain detected wave characteristics after the waves have been transmitted from one side of a medium (e.g., the tissue of a patient's finger) to the other. The wave characteristics that may be measured in accordance with present embodiments may include characteristics that relate predominantly to absorption of the emitted light in the probed medium (e.g., amplitude change) and characteristics that relate predominantly to scattering in the probed medium (e.g., phase shift). It should be noted that, as will be discussed further below, the correlation of certain wave characteristic (e.g., amplitude and phase) measurements to certain medium characteristics (e.g., quantity of scattering particles and blood oxygen saturation) may be based on high frequency modulation of the system's light sources, which generate the resolvable photon density waves.

As indicated above, the system 10 may be utilized to make measurements that relate predominantly to scattering in the observed volume. More specifically, the system 10 may be utilized to make measurements relating to a total amount of scattering particles in the observed volume based on phase shifts detected in the emitted light waves. For example, the system 10 may emit light that is modulated at a high frequency (e.g., 50 MHz to 3.0 GHz) to generate resolvable photon density waves, and then measure the phase shift of these high frequency waves to facilitate estimation of a total number of scattering particles in the observed medium. Similarly, as set forth above, the system 10 may be utilized to make measurements that relate predominantly to absorption in an observed volume. For example, the system 10 may detect changes in AC and DC amplitudes of the resolvable photon density waves to facilitate detection of a ratio of certain constituents in the blood (e.g., a ratio of oxygenated hemoglobin to total hemoglobin). It should be noted that the amplitude changes and phase shifts measured at a detection point may be considered relative to one or more points. For example, the amplitude and phase shifts measured at a detector may be considered relative to the associated values generated at the emitter.

Figure 2:
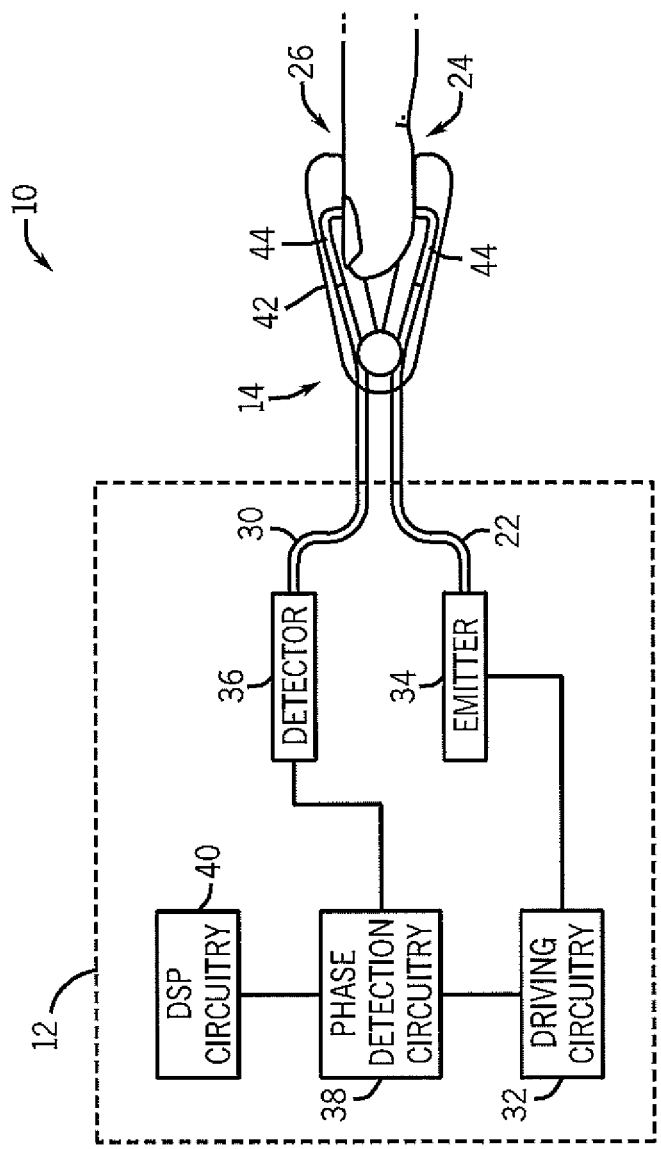
FIG. 2 illustrates a block diagram of a transmission mode pulse oximeter system capable of utilizing photon density waves in accordance with present embodiments.

FIG. 2 is a basic block diagram of an embodiment of the pulse oximeter system 10 that is capable of transmission mode photon density wave emission and detection. The configuration and operation of the system 10 in transmission mode may enable deep penetration of the photon density waves into a region of interest in a patient's tissue. As in FIG. 1, the system 10 illustrated in FIG. 2 includes the monitor 12 and the sensor 14. In FIG. 2, the monitor 12 and the sensor 14 include features capable of cooperating to transmit photon density waves into one side of a patient's tissue and out of a generally opposite side for detection. Specifically, in FIG. 2, the monitor 12 is illustrated as including various functional components that facilitate transmission of photon density waves through an emitter-side fiber optic cable 22 to the sensor 14. The sensor 14 is physically configured such that, when properly attached to a patient's tissue 24, the photon density waves from the emitter-side fiber optic cable 22 pass into one side of the patient's tissue 24 (e.g., one side of a patient's earlobe or finger), out of the generally opposite side of the patient's tissue 26, and into a detector-side fiber optic cable 30 coupled with the sensor 14. For example, the sensor 14 may include a clamping mechanism that positions the emitter-side fiber optic cable 22 generally opposite the detector-side fiber optic cable 30 when straddling the patient's tissue 24. In accordance with present embodiments, the sensor body 20 may be specifically arranged such that a light emission feature (e.g., the emitter-side fiber optic cable 22, a fiber optic component connector, a laser, or an LED) is generally arranged opposite a light detection feature (e.g., the detector-side fiber optic cable 30, a fiber optic component connector, a lens, a transparent layer, or a detector) such that photon density waves can be passed through the tissue 26 from the light emission feature on a first side of the tissue to the detection feature on a generally opposite or opposite side of the tissue 26.

The functional components disposed within or included as features of the monitor 12 may include sensor driving circuitry 32, an emitter 34, a detector 36, phase detection circuitry 38, and digital signal processing (DSP) circuitry 40. While some embodiments may include differing component arrangements (e.g., certain features may be included in the sensor 14 instead of the monitor 12), including these functional components within the monitor 12 may leave the sensor 14 to be generally composed of fiber optics, which may make the sensor 14 cheap and easily disposable. Indeed, the sensor 14 may include a sensor body 42 that houses fiber optic components 44 and/or portions of the emitter-side fiber optic cable 22 and the detector-side fiber optic cable 30. The fiber optic components 44 may include features (e.g., fiber optic curves and coupling mechanisms) that may facilitate communicative coupling with monitor 12 and/or arranging the emission and detection points of the emitter-side fiber optic cable 22 and the detector-side fiber optic cable 30 generally opposite one another and such that light is emitted substantially directly into the patient's tissue and detected opposite the emission point. As illustrated in FIG. 2, the emitter-side fiber optic cable 22 is coupled to the emitter 34 and the detector-side fiber optic cable 30 is coupled to the detector 36. Further, each fiber optic cable 22, 30 may be coupled to the sensor body 42 and/or the fiber optic components 44 within the body 42 to facilitate transmission of the photon density waves through the patient's tissue. In the illustrated embodiment, the fiber optic components 44 function to turn the emitted light into the patient's tissue 26 and the received light back into the detector-side fiber optic cable 30. In other embodiments, mirrors, prisms, the fiber optic cable itself or the like may be utilized to guide the light in a desired direction.

In operation, the driving circuitry 32 may generate waves (e.g., sine waves) and provide timing control signals such that the emitter 34 is activated in specified intervals and/or such that certain varying amplitudes of light are emitted by the emitter 34 to produce desired qualities of the photon density waves. The driving circuitry 32 may also include features that are capable of controlling access to the phase detection circuitry 38 via clock signals provided to the phase detection circuitry 38 from the driving circuitry 32. As an example of a typical process in accordance with present embodiments, the driving circuitry 32 may cause the emitter 34 to emit photon density waves at a high frequency into the emitter-side fiber optic cable 22 such that the photon density waves are transmitted into one side of the patient's tissue 24 and out of the other side of the patient's tissue 26. The detector-side fiber optic cable 30 may receive at least a portion of the photon density waves and transmit the photon density waves to the detector 36, which communicates with the phase detection circuitry 38 to identify phase information and so forth. This information may then be transmitted to the DSP circuitry 40 for analysis. It should be noted that in some embodiments, multiple emitters may be utilized in conjunction with multiple fiber optic cables or the multiple emitters may share a single fiber optic cable.

Figure 3:
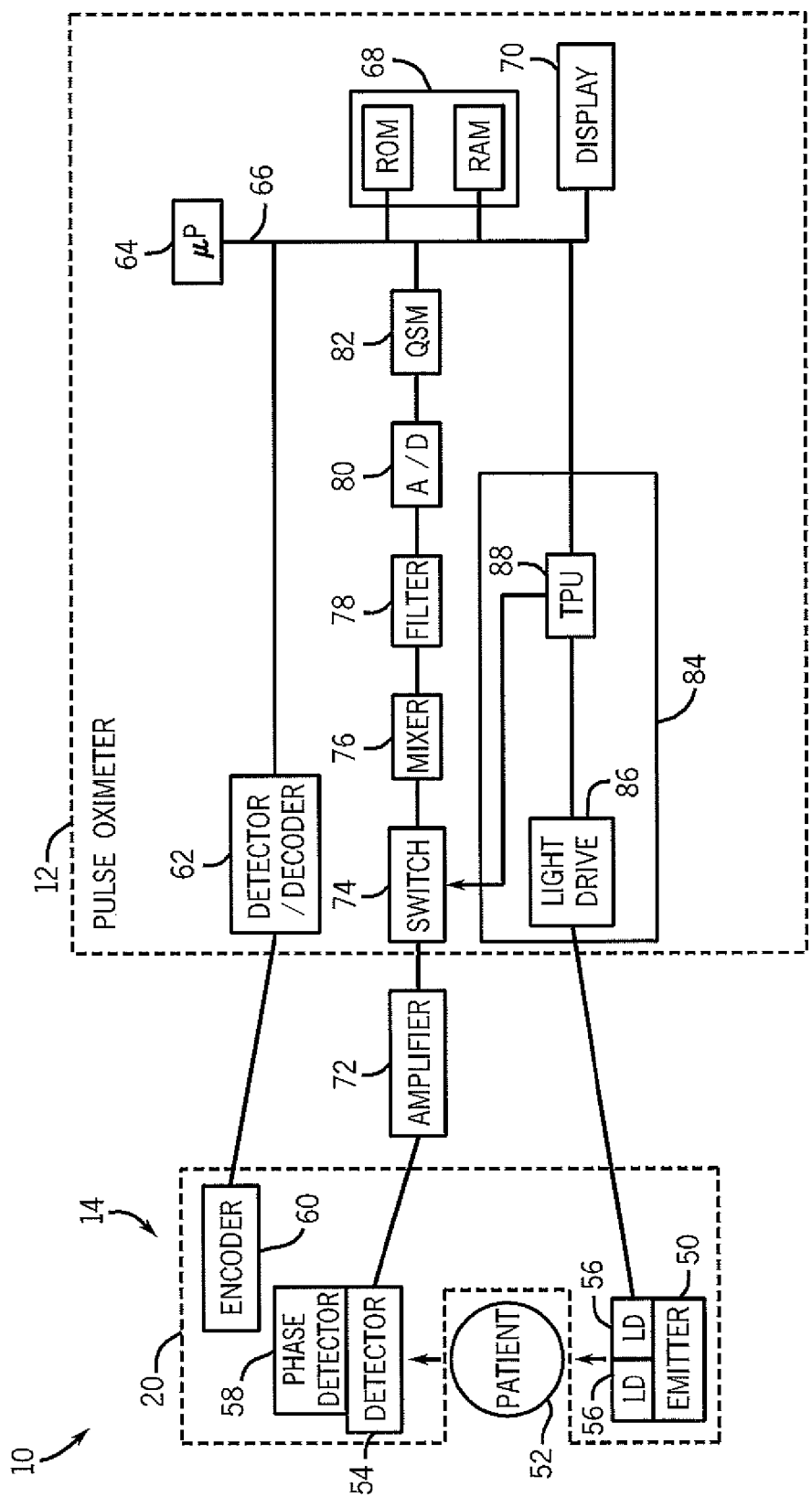
FIG. 3 illustrates a block diagram of a transmission mode pulse oximeter system capable of utilizing photon density waves in accordance with present embodiments.

FIG. 3 is a block diagram of another embodiment of the pulse oximeter system 10 that may be configured to implement embodiments of the present disclosure. As indicated above, the system 10 may include the monitor 12 and the sensor 14. In accordance with present embodiments, the sensor 14 may be configured such that light from an emitter 50 can pass into a patient's tissue 52 on one side and out a generally opposite side when properly attached. Further, the sensor 14 may be configured such that after being transmitted from one side of the tissue 52 to the generally opposite side, the light may be received by a photo-detector 54. The photo-detector 54 may then convert the received light into a photo-current signal, which may then be provided to the monitor 12. It should be noted that in some embodiments, multiple sensors 14 may be employed. Further, in some embodiments, one or more sensors may each include multiple emitters and/or detectors. If multiple emitters are employed, it will generally be desirable for each of the emitters to include red and infrared (IR) light sources, such as laser diodes (LD) 56.

In some embodiments, in addition to the emitter 50 and the detector 54, the sensor assembly or body 20 may also contain various other features in accordance with present embodiments. For example, the sensor 14 may include a phase detector 58 capable of detecting phase shifts in photon density waves observed by the detector 54. While the phase detection feature 58 is positioned within the sensor assembly 20 in the illustrated embodiment, in some embodiments, the phase detection feature 58 may be located within the oximeter 12. Additionally, the sensor 14 may include an encoder 60 (e.g., a resistor or chip) which may be capable of providing signals indicative of the wavelength(s) of light received from the emitter 50 to allow the oximeter 12 to select appropriate calibration coefficients for calculating oxygen saturation. The data or signal from the encoder 60 may be decoded by a detector/decoder feature 62 in the oximeter 12.

In some embodiments, the oximeter 12 may include a microprocessor 64 coupled to an internal bus 66. Also connected to the bus 66 may be a memory 68 (e.g., RAM and/or ROM) and a display 70. Received signals from the detector 54 may be passed through a first amplifier 72, a switch 74, an analog multiplier 76, a low pass filter 78, and/or an analog-to-digital converter 80. The digital data may then be stored in a queued serial module (QSM) 82 for later downloading to the memory 68 as the QSM 82 fills up. In an embodiment, there may be multiple parallel paths of separate amplifier, filter, and A/D converters for multiple light wavelengths or spectra received, and/or for phase data generated by the phase detector 58. In one embodiment, a signal from the phase detector 58 may be processed in any suitable manner, and may be sent through a different data path than the signal from the detector 54, which may be configured to detect amplitude of the photon density waves. The received optical signal may be converted into an electrical signal at the detector 54. The electrical signal may then be amplified by the amplifier 72 and sent to a frequency mixer or analog multiplier (e.g., analog multiplier 76) to generate a signal that is proportional to a phase difference between a reference oscillator (not shown) and the received signal. Similarly, the AC and DC amplitudes of the received signal may be determined with peak detection circuits and low pass filters (e.g., filter 78).

As illustrated in FIG. 3, the emitter 50 may include the two LDs 56. The LDs 56 may receive modulated drive signals from the monitor 12 that activate the LDs 56 and cause them to emit light at certain intervals. Thus, the monitor 12 may activate and deactivate the LDs 56 at high frequencies that may facilitate measurements relating to scattering in the probed medium based on phase changes in emitted photon density waves. This modulation function may be performed by a modulator 84. The modulator 84 may include a hardware feature, a software feature, or some combination thereof. For example, a portion of the modulator 84 may be stored on the memory 68 and may be controlled by the processor 64. In the illustrated embodiment, the modulator 84 includes a light driver 86 and a time processing unit (TPU) 88 that cooperate to modulate the light emissions of the LDs 56. The TPU 88, which may include a sine wave generator, may provide timing control signals to the light drive circuitry 86, which controls when the emitter 50 is activated, and if multiple light sources are used, the multiplexed timing for the different light sources. The TPU 88 may also control the gating-in of signals from the detector 54 through the first amplifier 72 and the switching circuit 74. These signals are sampled at the proper time, depending at least in part upon which of multiple light sources is activated, if multiple light sources are used.

In the illustrated embodiment, the modulator 84 is disposed in the monitor 12. However, in some embodiments the modulation function may be performed by a modulator disposed within the sensor 14. Indeed, it should be noted that in some embodiments, the features related to modulating and detecting the phase of the emitted light waves may be arranged within the system 10 to avoid potential interference. For example, high frequency modulation and detection features may be co-located within the sensor 14 to reduce the distance traveled by the signals, and, thus, reduce potential interference. Indeed, in a specific example, the sensor 14 may include a commercially available chip set for phase measurement and commonly available drive circuits (e.g., DVD R/W driver circuits) for high frequency modulation. Examples of such devices may include the AD8302 available from Analog Devices™ and the LMH6525 available from National Semiconductor™. In other embodiments the LDs 56 may be positioned within the monitor 12 and light may be transmitted from the LDs 56 in the monitor 12 to the sensor 14 via fiber optics to reduce potential interference.

Regardless of the modulator's location, in contrast to traditional pulse oximetry, which conducts measurements at sufficiently low frequencies (e.g., 1.5 KHz) to be considered DC, the modulator 84 may be configured to modulate the LDs 56 at sufficiently high frequencies (e.g., approximately 50 MHz to 3.0 GHz) to cause resolvable photon density waves to propagate through the tissue 52. In some embodiments, the modulator 84 may be configured to sweep a range from 50 MHz to 2.4 GHz. In some embodiments, the modulator 84 may be configured to modulate between 100 MHz and 1 GHz or to sweep a range from 100 MHz to 1 GHz. Thus, present embodiments operate at much higher frequencies than the traditional pulse oximetry sampling frequency of 1 sample every 67 microseconds.

In some embodiments, for continuous modulation of the LDs 56, resolvable amplitude and phase relationships of the photon density waves may be established at various positions from the emitter along the tissue bed 52. By modulating the light emitters at sufficiently high frequencies, the wavelengths of photon density waves may be shorter than the average distance required for light to be absorbed. Thus, the phase changes in the photon density waves can be attributed predominantly to scattering and not absorption. Further, in view of this, it can be determined that detected phase changes correspond to a number of scattering particles or volume change in the probed medium. The frequency of the photon density waves is essentially locked to the initial light source input and the phase change is essentially locked to arterial pulsation and the introduction of scattering particles. Indeed, the variation in AC scattering to DC scattering measured by phase offset may yield information about the total arteriole volume probed.

For a modulation frequency where the product of the frequency and the mean time between absorption events is much larger than 1, the change in phase between two points located a distance r from each other on a tissue bed may be given by the relation, $$\Delta\phi = r\sqrt{\frac{\omega\mu_s'}{6c}},$$

where c is the speed of light, ω is the angular frequency of modulation, and $\mu_s'$ is the reduced scattering coefficient. The reduced scattering coefficient for a tissue bed is comprised of both blood and surrounding tissue components. It can be written as, $\mu_s'\text{total} = V_{blood}\mu_s'\text{blood} + V_{tissue}\mu_s'\text{tissue}.$ The time varying component of this equation at a single wavelength will generally be only the portion due to arterial blood. The time varying component of this equation at a second wavelength will allow for the deconvolution of the scattering coefficient. The scattering coefficient for blood is related to the hematocrit (HCT) through the relation, $\mu_s'\text{blood} = \sigma_s(1-g)(HCT/V_i)(1-HCT)(1.4-HCT),$ where g is the anisotropy factor, σ is the scattering cross section of an erythrocyte, Vi is the volume of an erythrocyte and HCT is the hematocrit.

Accordingly, when the modulator 84 operates at a high enough frequency, measured phase changes in the photon density waves may be utilized to calculate a number of scattering particles in the observed volume. For example, the monitor 12 may be configured to receive phase shift and/or amplitude data from the sensor 14 and calculate a value related to a quantity of scattering particles in the probed tissue for display on the monitor 12. Specifically, the monitor 12 may include instructions or an algorithm stored on the memory 68 and configured to perform such calculations.

Figure 4A:
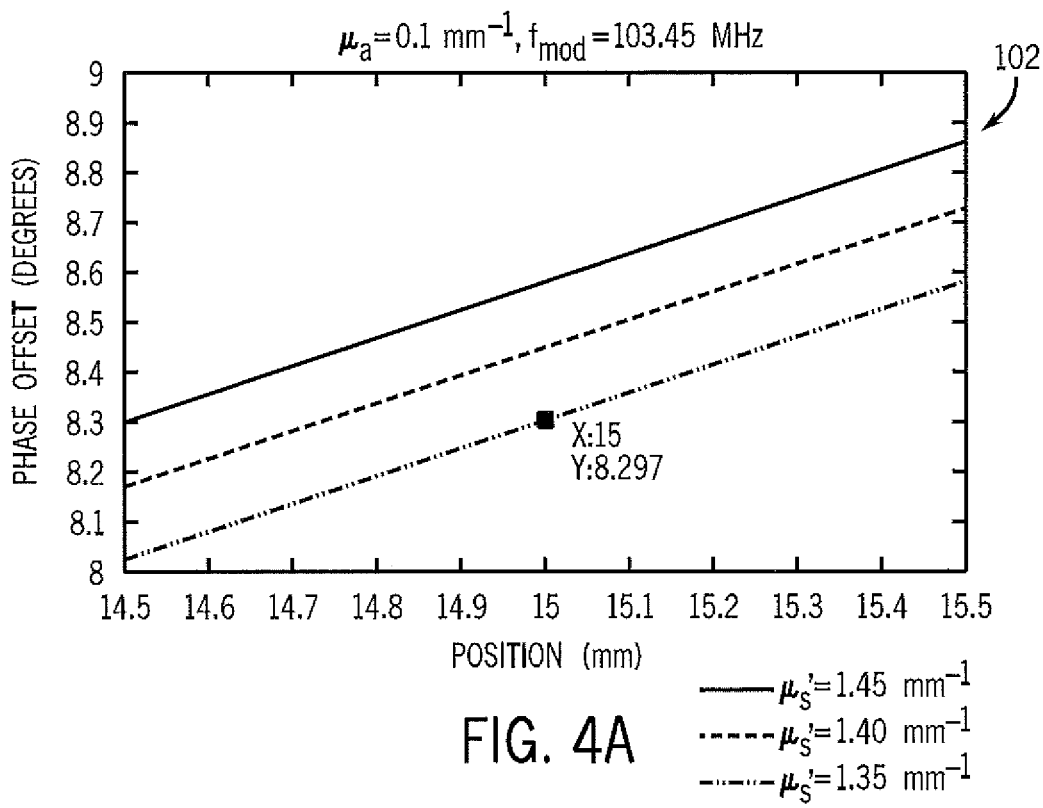
FIG. 4 illustrates a pair of graphs that represent simulations of phase changes in photon density waves modulated at high frequency, wherein the phase changes are due to scattering in accordance with present embodiments.
Figure 4B:
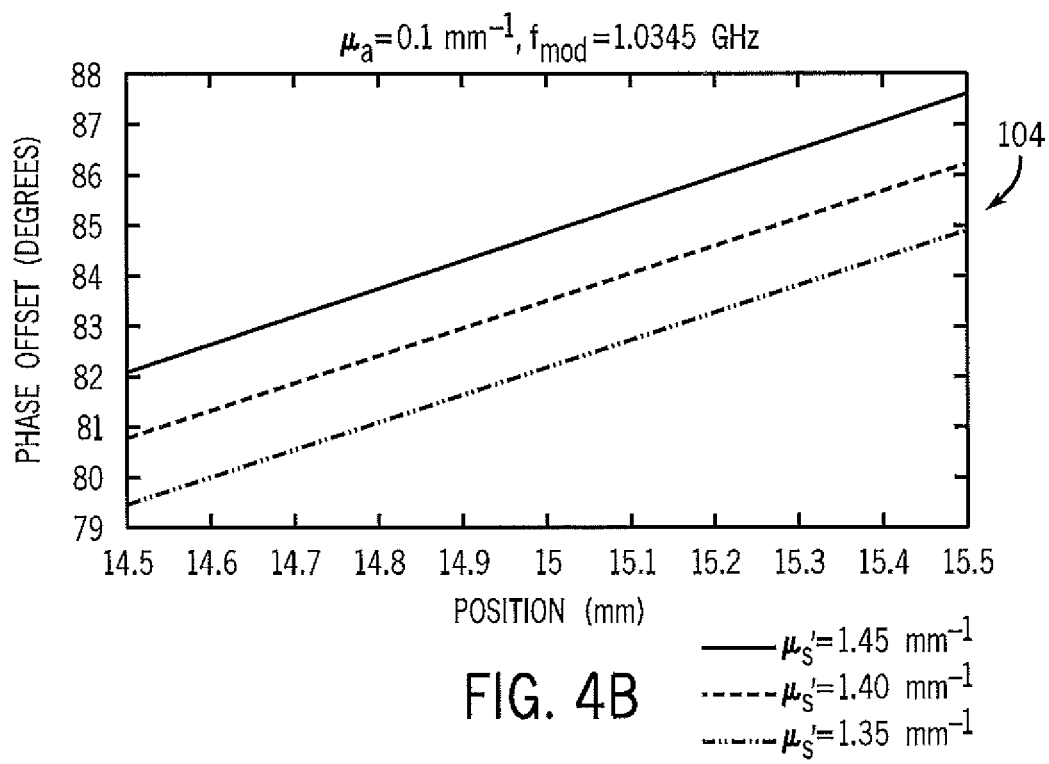

As an example of the correlation of phase change measurements of photon density waves modulated at high frequency to a number of scattering particles in the probed medium, FIGS. 4A and 4B include a pair of graphs that represent simulations of phase changes due to scattering at two different frequencies. Specifically, FIG. 4A includes a first graph 102 and FIG. 4B includes a second graph 104 that each represent simulations of phase change (measured in degrees) due to scattering variation of an arterial pulse (Hemoglobin 15 g/dL) for photon density waves at 890 nm that are modulated with a frequency of 103.4 MHz and 1.034 GHz respectively. It should be noted that the increase in frequency from 103.4 MHz in the first graph 102 to 1.034 GHz in the second graph 104 results in a phase change of approximately 3-4 degrees. This change correlates to the wavelengths of the photon density waves. In other words, because the wavelength is reduced even further from the 103.4 MHz modulation rate (first graph 102) to the 1.034 GHz modulation rate (second graph 104) and there is less opportunity for absorption, the phase change of the higher modulation rate corresponds more specifically to scattering. In some embodiments, a range of frequencies between those shown in FIGS. 4A and 4B may be swept through to profile the characteristics of the tissue at different photon density wave frequencies.

Scattering may be quantified based on phase change. Specifically, as set forth above, a modulation frequency where the product of the frequency and the mean time between absorption events is much larger than 1, the change in phase between two points may be given by the relation, $$\Delta\phi = r\sqrt{\frac{\omega\mu'_s}{6c}}.$$

Changes in phase due to arterial pulsation may be directly related to the change in scattering coefficient of the medium which is due to the change in the concentration of the number of erythrocytes. It should be noted that a second method for correlating the scattering changes from the phase could involve a calibration curve determined from tissue phantoms or clinical data.

Figure 5:
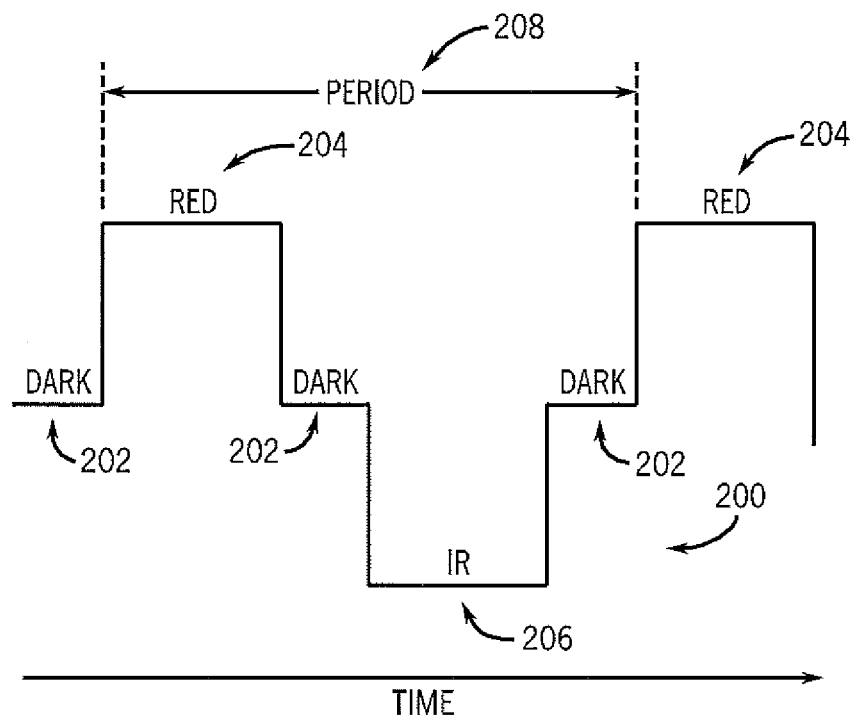
FIG. 5 illustrates an example of a source modulation signal in accordance with present embodiments.

FIG. 5 illustrates an example of a source modulation signal as driven by cross-coupled LEDs in accordance with some embodiments. Specifically, FIG. 5 illustrates a control signal 200 that may be generated by the modulator 84 to activate and/or deactivate an emitter including red and IR light sources, such as the LDs 56. In other embodiments, separate modulators may be utilized for each light source and/or additional light sources. Indeed, when multiple emitters are utilized, each emitter may be modulated by a separate modulator.

In the illustrated embodiment, the control signal 200 is representative of dark intervals 202, intervals of power 204 being supplied to a red LD, and intervals of power 206 being supplied to an IR LD over time. Further, the control signal 200 has a period designated by reference number 208. This period 208 may be adjusted such that each of the LDs 56 may be modulated with a desired frequency (e.g., approximately 100-1000 MHz) to generate photon density waves. Such adjustments to the modulation frequency may facilitate detection of phase shifts in the photon density waves, and, thus, variations in scattering based on such phase shifts. As may be appreciated by those of ordinary skill in the art, the control signal 200 may be adjusted or modified for different scenarios. For example, the control signal 200 may be adjusted to be generally sinusoidal, adjusted to include various intensity levels, and so forth. The sinusoidal nature of the wave may be controlled by a wave generator and the intensity levels may be adjusted by providing more power and/or by reducing dark intervals and increasing the length of time that light is emitted.

As indicated above, the phase of the photon density waves may be sensitive to changes in the scattering coefficient, while the amplitude of the photon density waves may be sensitive to the concentration of absorbers in the medium. Specifically, with regard to amplitude measurements, the AC amplitude and DC amplitude may yield information about absorption in the volume. Thus, detection of amplitude changes in the photon density waves may be utilized to calculate absorber concentration values in the observed medium, such as blood oxygen saturation values. Such calculations may be made using the standard ratio of ratios (i.e., ratrat) technique for the constant and modulated values of the photon density wave amplitudes at two wavelengths. Once the ratio of ratios values is obtained, it may be mapped to the saturation from clinical calibration curves.

With regard to phase shift measurements, when the wavelengths of the photon density waves get below that of the mean absorption distance, the phase becomes almost exclusively a function of the scattering coefficient. While dependent upon the tissue bed being probed, this is generally believed to occur at a modulation frequency in the range of approximately 500 MHz. Thus, the phase shift measurement may yield information about the number of erythrocytes or red blood cells in the local probed volume. The HCT discussed above is proportional to the number of erythrocytes. Accordingly, by sweeping frequencies, a multi-parameter output may be obtained that relates to standard pulse oximetry measurements as well as the puddle hematorcit.

The amplitude and phase at a given frequency may be proportional to the scattering and absorption coefficient at a given wavelength until the product of the frequency and the mean time between absorption events is much larger than 1. When the product of the frequency and the mean time between absorption events is much larger than 1, the amplitude is a function of the absorption and phase is only a function of the scattering. Thus, a frequency sweep may be used to reduce the error in the determination of a single value of reduced scattering coefficient for the blood and a single value of absorption coefficient. Indeed, in some embodiments, the amplitude and phase information may be utilized together to yield a value of total hemoglobin per unit volume.

In some embodiments, by modulating the light sources at a sufficient frequency, and, thus, facilitating a detectable phase shift that corresponds to scattering particles, present embodiments may provide an extra degree of certainty for blood flow parameter measurements. Indeed, the detected amplitude for the photon density waves may be utilized to calculate traditional pulse oximetry information and the phase may be utilized to confirm that such values are correct (e.g., within a certain range of error). For example, the amplitude information may be utilized to calculate a blood oxygen saturation ($SpO_2$) value and empirical data may indicate that a particular $SpO_2$ value should correspond to a particular phase variation at a given frequency. In other words, there may be a certain phase change that should accompany a given increase in absorber observed as a change in amplitude. Various algorithms (e.g., learning based algorithms such as support vector machines, cluster analysis, neural networks, and PCA) based on the measured phase shift and amplitude change may be compared to determine if the amplitude shift and phase shift correlate to a known $SpO_2$. If both the measured amplitude shift and phase shift correlate to a known $SpO_2$, the measured $SpO_2$ value may be deemed appropriate and displayed or utilized as a correct $SpO_2$ value. Alternatively, if the measured amplitude shift and phase shift do not agree, the calculated $SpO_2$ value may be identified as being corrupt or including too much noise and, thus, be discarded.

Figure 6:
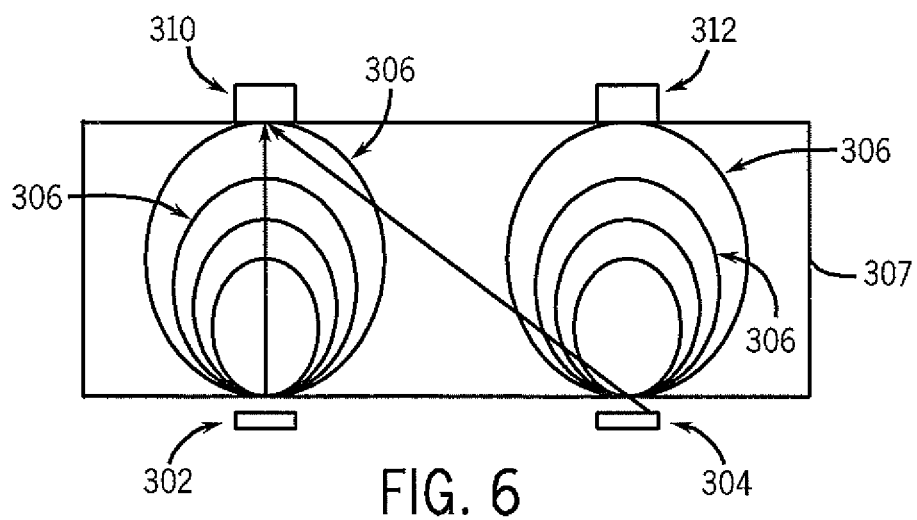
FIGS. 6-8 include representative diagrams of a multiple emitter and/or detector arrangements being utilized in conjunction with one another in accordance with present embodiments.
Figure 7:
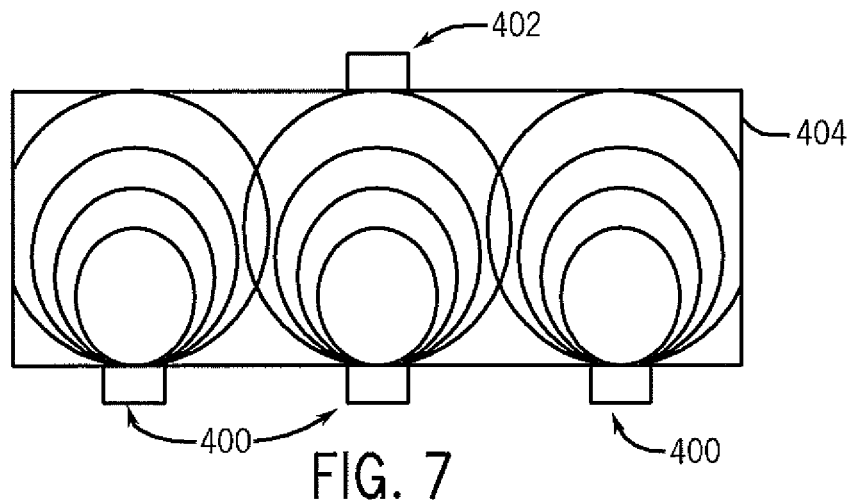
Figure 8:
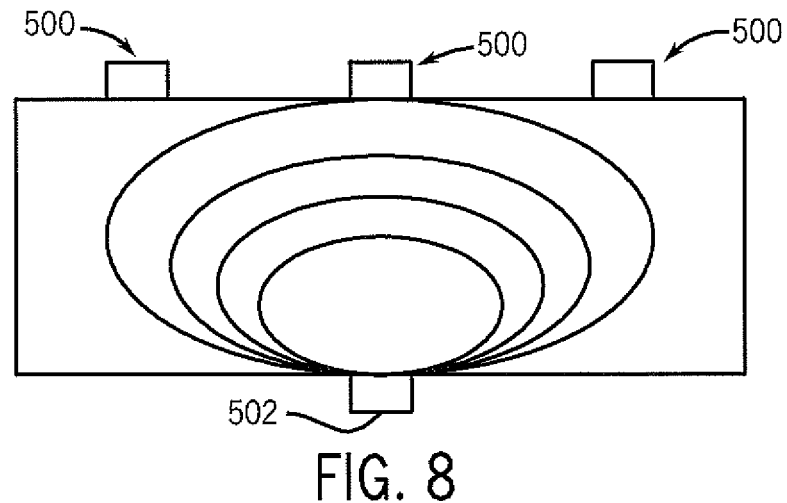

In some embodiments, as illustrated by FIGS. 6-8, multiple emitter and/or detector arrangements may be utilized in conjunction with one another to provide a transmission mode photon density wave system. Specifically, FIG. 6 illustrates a first emitter 302 and a second emitter 304, wherein each of the emitters 302, 304 includes a red and an IR light source (e.g., LED). Waves 306 represent photon density waves propagating through tissue 307 from the emitters 302, 304 to a first detector 310 and a second detector 312. During transmission mode operation, the emitters 302, 304 are positioned on a first side of the tissue 307 and the detectors are positioned on a second side of the tissue 307 generally opposite the first side. As will be understood by one of ordinary skill in the art, because the multiple emitters are generating separate waves in the same tissue bed, the waves can be made to interfere with one another by adjusting the modulation frequencies of each emitter 302, 304. Further, it should be noted that the transmission mode setup enables deep penetration to facilitate access to many different regions of interest. Accordingly, multiple emitters may be utilized to steer intensities through the tissue and adjust intensity patterns in the different areas of tissue. For example, the phase of the photon density waves could be adjusted in such a way as to completely cancel out any signal at the first detector 310. Thus, if the first detector 310 detects a signal, it may be an indication of noise.

FIG. 7 illustrates an embodiment including multiple emitters 400 and a single detector 402 positioned adjacent a patient's tissue 404. During transmission mode operation, the emitters 400 are positioned on a first side of the tissue 404 and the detector 402 is positioned on a second side of the tissue 404 generally opposite the first side. This embodiment may be utilized to generate an adaptive constructive/destructive interference pattern in the tissue bed, including deep within the tissue bed, by adjusting the relative phases of the emitters (at a given wavelength) that would allow for the measurement of local tissue components. These would be visible in the phase and amplitude changes determined by the single detector.

In other embodiments utilizing multiple emitters, the interference of photon density waves may facilitate sweeping photon density waves through a probed volume by changing the relative phase between the emitters. For example, such techniques may be utilized to establish a "phased array" of photon density waves for use in pulse oximetry and hemometry techniques. Indeed, such a "phased array" technique may facilitate identification of regions rich with pulsatile signals in the probed tissue and/or calibration of a sensor through the interference of photon density waves. For example, the phases of individual waves may be controlled to determine the intensity profile within the medium.

It may be desirable to detect regions rich with pulsatile signals to facilitate obtaining a strong pulsatile signal. For example, it may be desirable to focus on a specific location in tissue that includes an artery or even a specific portion of the artery. The transmission mode arrangement may facilitate access to such specific locations by enabling deep penetration. Periodic sweeps may be performed to insure that the focus remains on the pulsation-rich regions. Further, such a technique may define an adaptive measurement system that may be utilized to identify regions of low saturation and/or regions in the probed tissue where blockage may result in anemic conditions. Additionally, it is believed that the use of multiple emitters may facilitate adaptation of the sensor to different physiological variations between patients, such as different skin and/or tissue characteristics.

FIG. 8 illustrates an embodiment including multiple detectors 500 and a single emitter 502 capable of emitting and detecting photon density waves passed through tissue 504. During transmission mode operation, the emitter 502 may be positioned on a first side of the tissue 504 and the detectors 500 may be positioned on a second side of the tissue 504 generally opposite the first side. The illustrated embodiment may be utilized to identify non-physiological artifact. Each of the multiple detectors 500 may have a different phase and amplitude relationship with respect to each other. Uncorrelated changes in phase and amplitude between the multiple detectors 500 would result in a non-physiological artifact such as noise artifact, sensor off, and so forth.

The inclusion of multiple detectors around a tissue bed may facilitate detection of and/or compensation for a variety of noise artifacts that typically plague existing pulse oximetry technologies. Indeed, for a given wavelength, a time-varying phase and amplitude relation between multiple detectors may be established which is correlated to arterial pulse. The phase and amplitude information may form a phase space that yields a bounded parameter space for a single wavelength that contains physiological measurements. Noise artifacts will typically lie outside of this bounded area, as will be discussed in further detail below. Further, the addition of a second wavelength may facilitate formation of a 4-dimensional physiological measurement space that facilitates noise artifact reduction due to constraints of decision planes in the hyperspace. Correlated phase and amplitude changes for a single wavelength are bounded by physiological parameters such as arteriole density, realistic hematocrit numbers, and so forth. At a single wavelength, these bounds result in bounds on the detected amplitude and phase in a 2D space. These same bounds are applicable for a second wavelength. The 4 factor correlation (phase(wavelength1), phase wavelength2), amplitude(wavelength1), amplitude(wavelength2)) is bounded by physiological factors in a linked 4D space. The bounds can be drawn as hyperplanes in that space. For example, cluster analysis, Neural Networks, and partial least squares (PLS) algorithms may be used to generate the decision planes and compensate for a variety of noise artifact.

Figure 9:
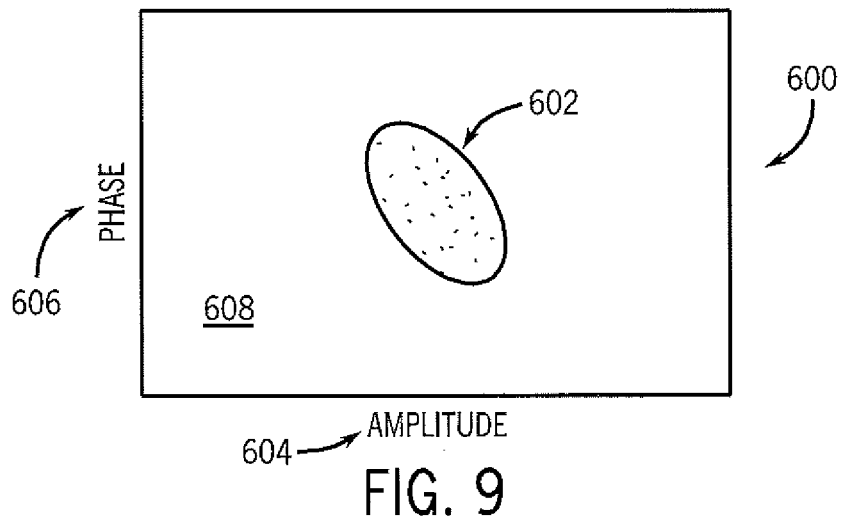
FIG. 9 illustrates a 2-dimensional plot that represents a physiological state characterized by amplitude and phase shifts in accordance with present embodiments.

In some embodiments, and as an example, FIG. 9 includes a 2-dimensional plot 600 that represents a physiological state 602 characterized by amplitude 604 and phase shifts 606. Once phase shift and/or amplitude data has been properly characterized based on empirical data, certain correlations may be indicative of a change in pressure (e.g., a sensor is attached too tightly), a certain area of tissue being subject to exsanguination, a sensor being off noise being present, and so forth. The plot 600 is representative of a single wavelength at a given frequency. Thus, multiple wavelengths at a given frequency would each have this type of physiological space for expected amplitude and phase variation. Noise artifact 608 will generally lie outside of this bounded parameter space or physiological regime. Accordingly, if a measurement falls outside of the physiological regime, it may be discarded as including too much noise. When a measurement is discarded, it may be replaced with the previous measurement or some combination of historical values. For example, historical values may be averaged using an averaging routine to provide a replacement for the noisy current measurement value.

What is claimed is:

1. A monitoring system, comprising:
   a modulator configured to modulate light to generate photon density waves at a modulation frequency generally in a range of 50 MHz to 3 GHz;
   one or more configured to be emission features disposed on a first side of a tissue of a patient and configured to emit the photon density waves into the first side of the tissue;
   one or more detection features configured to be disposed on a second side of the tissue, generally opposite the first side, and configured to receive the photon density waves at the second side of the tissue, wherein at least one of the one or more detection features is directly aligned with at least one of the one or more emission features;
   one or more detectors respectively communicatively coupled with the one or more detection features, wherein the one or more detectors are configured to detect characteristics of the photon density waves comprising amplitude changes and phase shifts; and
   a processor configured to make determinations relating to a value of a physiologic parameter of the tissue based at least in part on the detected characteristics.

2. The system of claim 1, wherein each of the one or more detection features comprises a respective fiber optic cable communicatively coupled to the at least one detector.

3. The system of claim 2, wherein each of the one or more detection features comprises a respective curved fiber optic component, and wherein the respective curved fiber optic components are communicatively coupled to the respective fiber optic cables of the one or more detection features.

4. The system of claim 1, wherein the one or more emission features comprise a fiber optic cable communicatively coupled with an emitter.

5. The system of claim 1, wherein the one or more emission features comprise a laser, a lens, or a transparent layer.

6. The system of claim 1, wherein the modulator, the detector, and the processor are disposed within a monitor, and wherein the one or more emission features and the one or more detection features are disposed within a sensor.

7. The system of claim 1, wherein the processor is configured to reject or accept the determined value of the physiologic parameter based on whether calculations based at least in part on the relative characteristics are complimentary.

8. The system of claim 1, wherein the modulator is configured to modulate the light at approximately 100 MHz to 1 GHz.

9. The system of claim 1, wherein the processor is configured to calculate an estimated number of scattering particles in the tissue based at least in part on detected phase shifts.

10. The system of claim 1, wherein the modulator is configured to modulate the light to generally sweep the tissue with a plurality of modulation frequencies.

11. The system of claim 1, wherein the processor is configured to determine a presence of noise based on a particular detection feature of the one or more detector features receiving the photon density waves.

12. A method, comprising:
    modulating light at a modulation frequency in a range of 100 MHz to 3 GHz to generate photon density waves;
    transmitting the photon density waves into a first side of a medium using a plurality of emitters;
    detecting the photon density waves from a second side of the medium, opposite the first side, using a plurality of detectors, wherein at least one of the plurality of detectors is disposed directly across from at least one of the plurality of emitters;
    identifying relative amplitude changes and phase shifts in the detected photon density waves using a processor; and
    detecting and graphically indicating a physiologic value related to scattering particles in the medium based at least in part on the amplitude changes, or phase shifts, or combinations thereof.

13. The method of claim 12, comprising transmitting the photon density waves into the first side of the medium via a plurality of fiber optic cables coupled to the plurality of emitters.

14. The method of claim 12, comprising receiving the photon density waves from the second side of the medium via a plurality of fiber optic cables respectively coupled to the plurality of detectors and detecting the photon density waves with the plurality of detectors.

15. The method of claim 12, comprising modulating the light at approximately 100 MHz to 1 GHz.

16. The method of claim 12, comprising discarding a portion of the photon density waves as noise when the portion of the photon density waves is detected by a particular detector of the plurality of detectors.

17. A system, comprising:
    a light source configured to modulate light at different frequencies to generate photon density waves, wherein the different frequencies generally range from approximately 100 MHz to 1 GHz;
    an emission feature configured to emit the photon density waves from the light source into a medium;
    a plurality of detection features configured to be disposed on an opposite side of the medium and configured to receive the photon density waves, wherein at least one of the plurality of detection features is aligned with the emission feature;
    a plurality of detectors coupled to the plurality of detection features and configured to detect relative characteristics of the photon density waves at the plurality of detection features after the photon density waves transmiss at least a portion of the medium; and
    a processor configured to coordinate the modulation of the light source to establish coordinated wave characteristics and configured to calculate values for physiologic features or parameters of the medium based at least in part on the relative characteristics.

18. The method of claim 17, wherein the emission feature and the plurality of detection features comprise a plurality of fiber optic cables.

19. The method of claim 17, wherein the coordinated wave characteristics comprise focused wave intensity in a specified region of the medium.

20. The method of claim 17, wherein the processor is configured to determine a presence of noise in the photon density waves based on a particular detector of the plurality of detectors receiving a portion of the photon density waves.

* * * * *